United States Patent
Schauperl et al.

(10) Patent No.: US 7,661,322 B2
(45) Date of Patent: Feb. 16, 2010

(54) PIEZOELECTRIC SENSOR DEVICE WITH SENSOR HOUSING AND HOLDER FOR HOLDING A PIEZOELECTRIC SENSOR ELEMENT

(75) Inventors: Richard Schauperl, Leibnitz (AT); Peter Prenninger, Graz (AT); Johannes Macher, Graz (AT)

(73) Assignee: AVL List GmbH, Graz (AT)

( * ) Notice: Subject to any disclaimer, the term of this patent is extended or adjusted under 35 U.S.C. 154(b) by 0 days.

(21) Appl. No.: 11/905,855

(22) Filed: Oct. 4, 2007

(65) Prior Publication Data
US 2008/0083284 A1    Apr. 10, 2008

(30) Foreign Application Priority Data
Oct. 9, 2006    (AT) .............................. A 1678/2006

(51) Int. Cl.
*G01N 3/02*    (2006.01)
(52) U.S. Cl. ....................................................... 73/856
(58) Field of Classification Search .................... 73/856
See application file for complete search history.

(56) References Cited

U.S. PATENT DOCUMENTS

| | | | | |
|---|---|---|---|---|
| 4,429,247 A | * | 1/1984 | Feldman | 310/322 |
| 4,701,660 A | * | 10/1987 | Baumgartner et al. | 310/338 |
| 5,031,460 A | | 7/1991 | Kanenobu et al. | |
| 5,753,798 A | * | 5/1998 | Engeler et al. | 73/35.13 |
| 6,029,500 A | * | 2/2000 | Tom | 73/31.05 |
| 6,972,841 B2 | | 12/2005 | Krempl et al. | |
| 2005/0150305 A1 | | 7/2005 | Oboodi et al. | |
| 2006/0141608 A1 | * | 6/2006 | Aastrup et al. | 435/287.1 |

FOREIGN PATENT DOCUMENTS

| | | |
|---|---|---|
| EP | 0394540 | 10/1990 |
| EP | 0768532 | 4/1997 |
| GB | 2019581 | 10/1979 |
| GB | 2073423 | 10/1981 |

OTHER PUBLICATIONS

English Abstract of EP 0394540, Oct. 31, 1990.

* cited by examiner

*Primary Examiner*—Lisa M Caputo
*Assistant Examiner*—Octavia Davis
(74) *Attorney, Agent, or Firm*—Dykema Gossett PLLC

(57) ABSTRACT

A piezoelectric sensor device, especially for use with a microbalance, with a sensor housing and a holder for holding a piezoelectric sensor element. In order to permit quick exchange of crystals and to minimize the size of the assembly, the holder is configured as a clamping element which has at least one elastic first arm for clamped holding of the contact region of the essentially strip-shaped piezoelectric resonator element, whose measuring region is subjected to a fluid stream to be measured.

18 Claims, 4 Drawing Sheets

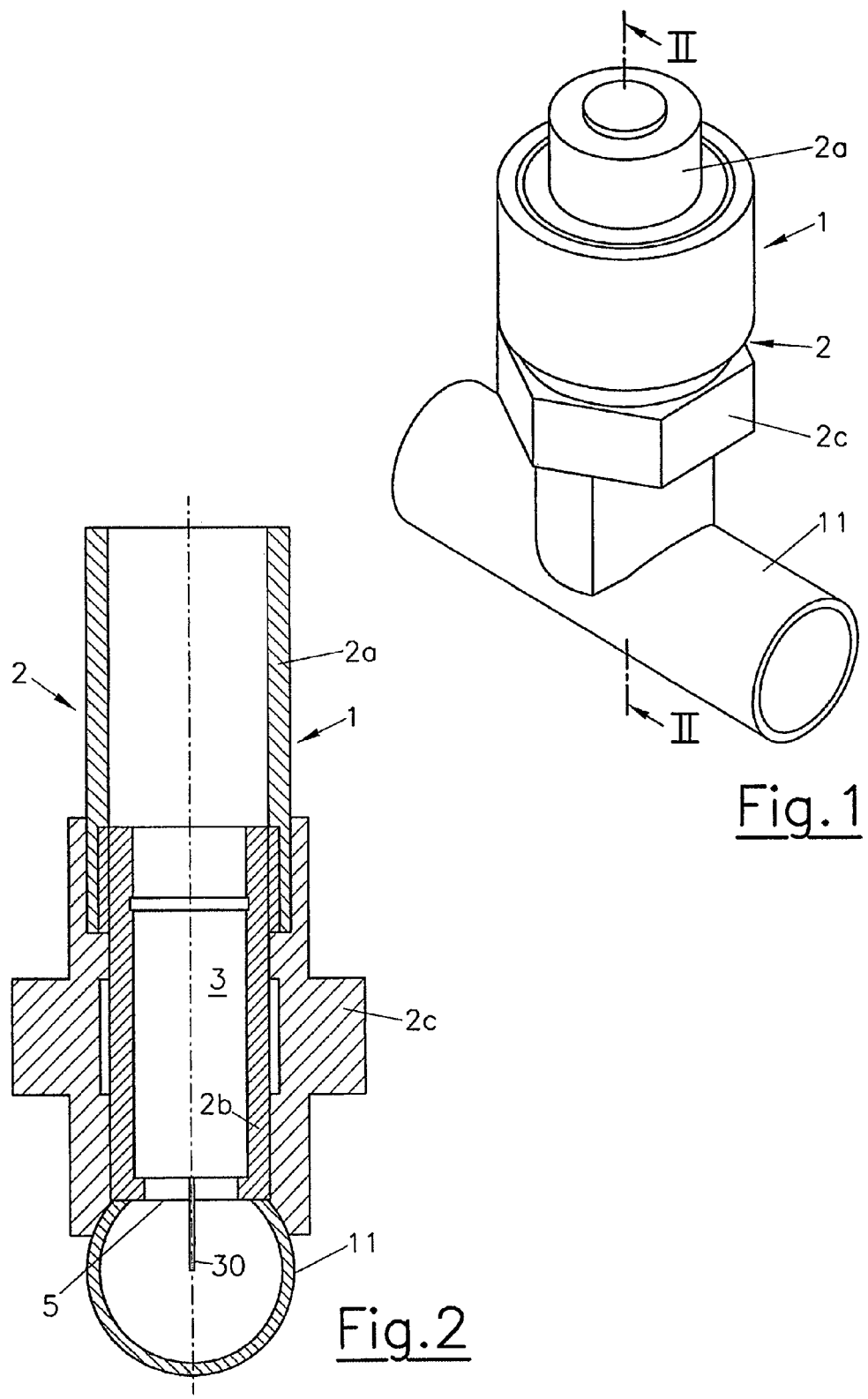

PIEZOELECTRIC SENSOR DEVICE WITH SENSOR HOUSING AND HOLDER FOR HOLDING A PIEZOELECTRIC SENSOR ELEMENT

BACKGROUND OF THE INVENTION

The invention relates to a piezoelectric sensor device, especially for use with a microbalance, with a sensor housing and a holder for holding a piezoelectric sensor element.

DESCRIPTION OF THE PRIOR ART

Known piezoelectric sensor devices, for instance for measuring exhaust gas samples, are furnished with piezoelectric resonator elements with circular cross-section, which are held in a special high-temperature holder for crystals of circular design. Rapid exchange of the crystals subject to the fluid stream will not be possible, however, with this kind of holder. Besides, the circular crystal design is relatively space-consuming (see for instance EP 1 316 796 A1).

There are known holders for pressure and force sensors, which are not suitable for receiving a resonator element, however. EP 0 394 540 B1, for instance, discloses a holder for a tubular piezoelectric pressure sensor, in which a small piezo-ceramic tube is clamped between a membrane and a holder. From DE 40 02 790 A1 a sensor pick-up for determining pressure changes in pipes is known, in which a piezoelectric element is mounted on the outer perimeter of a pipe by means of a clamping device. The piezoelectric element in this case is not in contact with a fluid stream.

From EP 0 768 532 A2 an acceleration sensor with a two-part piezoelectric element is known. Bending of the sensor element due to acceleration forces causes a voltage change in the piezoelectric element. A resonator application is not disclosed.

U.S. Pat. Appl. 2005/0150305 A1 describes a measuring apparatus with a sensor rod clamped on one end, which under mechanical load emits a signal proportional to the load. The piezo-resistive effect is used in connection with a bridge circuit.

SUMMARY OF THE INVENTION

It is the object of the present invention to avoid the above mentioned disadvantages and to enable rapid exchange of the piezoelectric sensor element in a sensor device as described above.

In the invention this object is achieved by providing that the holder is configured as a clamping element, which has at least one elastic first arm for clamping the contact region of an essentially strip-shaped, piezoelectric resonator element, whose measuring area is subjected to the fluid stream to be measured, the said clamping element having a non-elastic second arm, for instance. The strip-shaped resonator element may be exchanged by removing it together with the holder from the sensor housing.

The first and the second arm—both might also be elastic—are at a distance from each other, such that the resonator element may be inserted between the first and second arm of the holder.

It may be provided that the first and the second arm protrude in axial direction from a preferably cylindrical base plate.

It will be a special advantage if the holder can be inserted, at least partly, into a preferably cylindrical guiding and protecting element.

The sensor housing may consist of more than one part, it may for instance have a first and a second sensor housing part, which are preferably joined by a threaded connection. In a first variant the guiding and protecting element can be inserted into the sensor housing, preferably a hollow, cylindrical second sensor housing part.

Alternatively it is possible that the guiding and protecting element is inserted, preferably glued, into the bore of a ring, preferably a ceramic ring, and that the ring is inserted in a second sensor housing part of the sensor housing.

In this case it may be provided that the guiding and protecting element is partly located in a third sensor housing part, preferably configured as a welding nipple, which third part is joined to a second sensor housing part receiving the ring.

In a second variant of the invention the holder and the guiding and protecting element are glued into a ceramic ring. The surfaces of the ring are used as sealing surfaces.

In this variant the sensor housing consists of a first, a second and a third sensor housing part. The second sensor housing part is joined to the third sensor housing part, for instance by welding.

The guiding and protecting element together with the ring is inserted in the second sensor housing part. The third sensor housing part is configured as a welding nipple and is welded into a pipe system. The first housing part in this case is a covering cap, which may be screwed onto the second housing part.

In order to securely grip the resonator element it is advantageous if the first and/or the second arm of the clamping device is curved. The holder is advantageously made of machinable glass ceramics, which has no porosity. It provides lateral contacting and stabilizes the resonator element, which advantageously is a $GaPO_4$ strip resonator. Due to the spring action of the first arm of the clamping element temperature changes will not affect the functioning of the holder. The holder, which is especially designed for strip resonators, may be adapted to the size of the inserted strip resonator. The holder is gas-tight and high-temperature-resistant.

Like the holder the guiding and protecting element may be made of glass ceramics. The holder is inserted into the interior of the cylindrical guiding and protecting element. Thus the holder and the resonator are guided and protected against exterior influences.

The sensor housing consists of a plurality of metal parts, for instance two or three. These parts position the guiding and protecting element, the holder and the resonator element in the gas stream to be measured and provide gas-tight sealing. The metal parts are joined by a threaded connection.

The sensor housing is attached to a pipe system by a gas-tight welded cutting-ring fitting.

BRIEF DESCRIPTION OF THE DRAWINGS

The invention will be further described below, with reference to the enclosed drawings, wherein FIG. 1 shows an oblique view of a sensor device according to the invention in a first variant, FIG. 2 shows the sensor device in a longitudinal section along line II-II of FIG. 1.

DETAILED DESCRIPTION OF THE PREFERRED EMBODIMENTS

Figure 3:
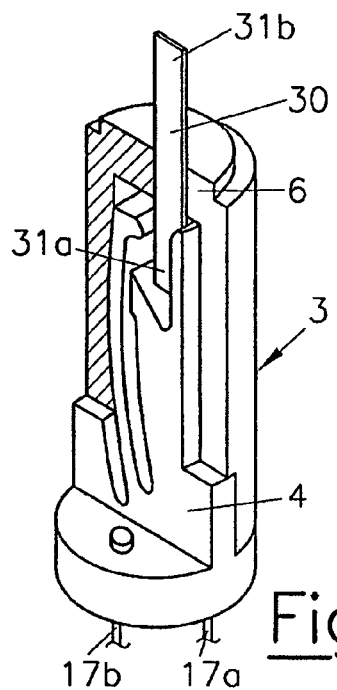
FIG. 3 shows an oblique view of a partially cut guiding and protecting element with holder and sensor element.

FIG. 1 and FIG. 2 show a piezoelectric sensor device 1 with a sensor housing 2, comprising a first sensor housing part 2a and a second sensor housing part 2b, where the cap nut has been omitted in FIG. 2. The metal sensor housing parts 2a, 2b position in a gas-tight manner a cylindrical guiding and protecting element 3 in a gas stream to be measured. The guiding and protecting element 3 receives a holder 4 (see FIG. 3 to FIG. 5) for a sensor element 30 configured as a strip-shaped resonator element (strip resonator), which is shown in detail in FIG. 13 and FIG. 14. The resonator element 30 is exposed to the gas stream to be measured via an opening 5 in the lower sensor housing part 2b and a slit 6 in the cylindrical guiding and protecting element 3 (FIG. 6).

Figure 4:
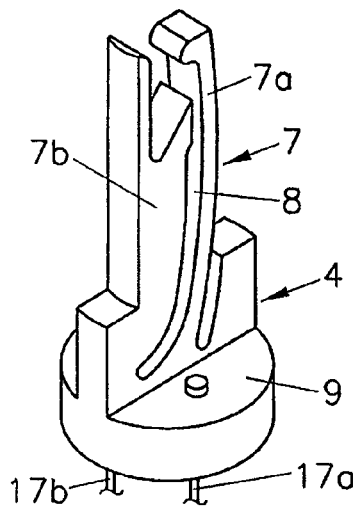
FIG. 4 shows a holder of the sensor device in an oblique view.
Figure 5:
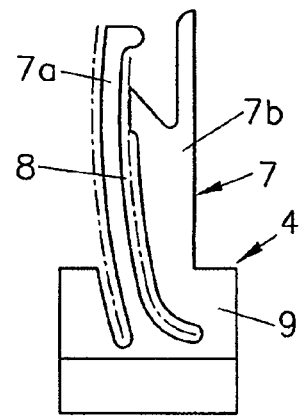
FIG. 5 shows the holder in a side view.
Figure 6:
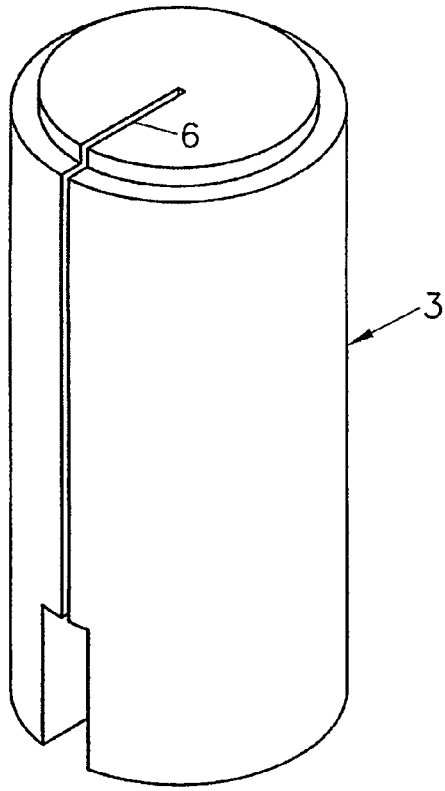
FIG. 6 shows a guiding and protecting element in an oblique view.

FIGS. 3 to 5 show the holder 4 in detail. The high-temperature-resistant holder 4 is furnished with a clamping element 7, which comprises an elastic arm 7a and a non-elastic arm 7b. Between the elastic first arm 7a and the non-elastic second arm 7b there is provided a slot 8, which will receive the sensor element 30. The two arms 7a and 7b are placed on an essentially circular base plate 9. The material of the holder assembly is machinable glass ceramics, which has no porosity. The holder assembly stabilizes and provides lateral contacting for the sensor element 30, which is formed by a $GaPO_4$ strip resonator. Due to the spring action of the first arm 7a of the clamping element 7 this function is also upheld in the instance of temperature changes. The holder 4 is provided with an electrically conductive coating, for instance a platinum coating, with the coated regions of the two arms 7a and 7b being electrically separated and connected to electrical leads 17a, 17b.

Figure 7:
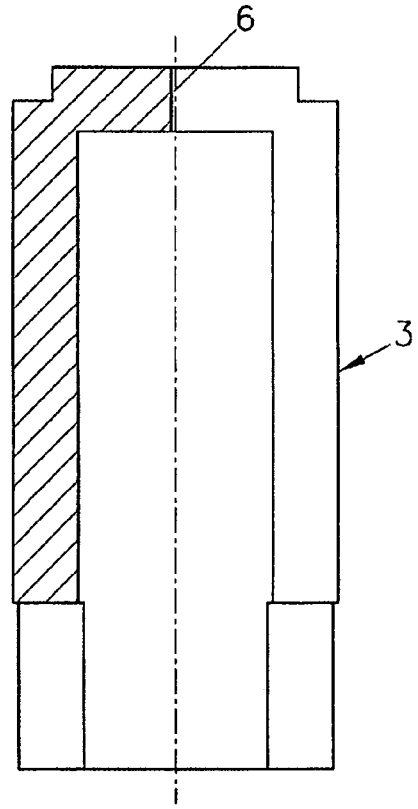
FIG. 7 shows the guiding and protecting element in a longitudinal section.
Figure 8:
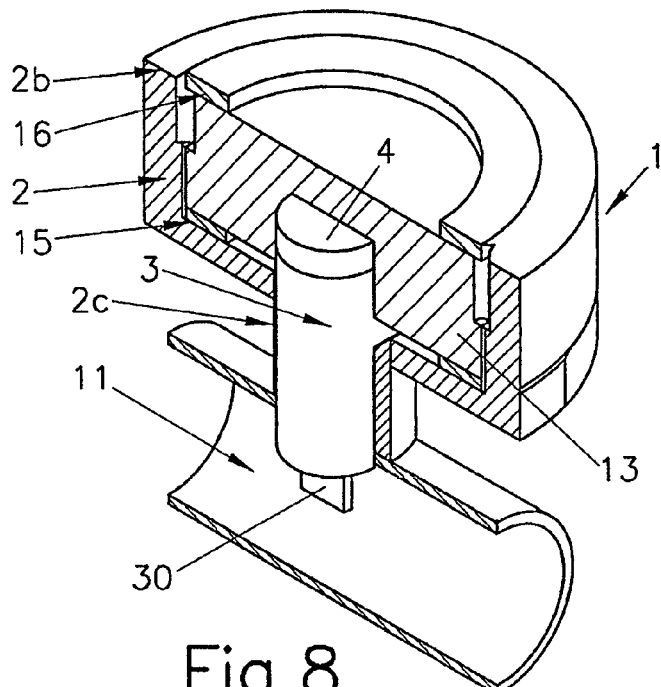
FIG. 8 shows an oblique view of a second variant of the sensor device according to the invention attached to a pipe system.
Figure 9:
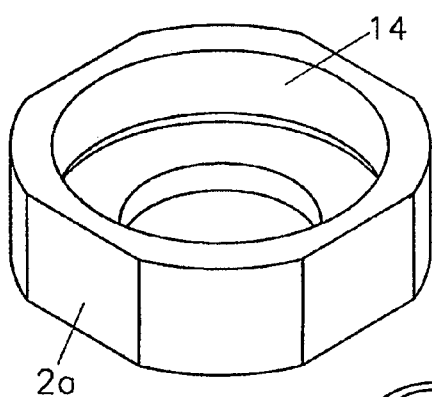
FIG. 9 shows a first sensor housing part of the sensor device of FIG. 8 in an oblique view.
Figure 10:
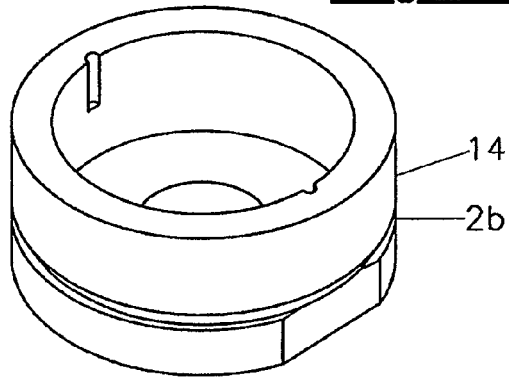
FIG. 10 shows a second sensor housing part of the sensor device of FIG. 8 in an oblique view.
Figure 11:
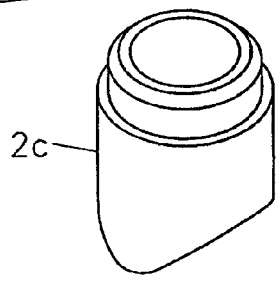
FIG. 11 shows a third sensor housing part of the sensor device of FIG. 8 in an oblique view.
Figure 12:
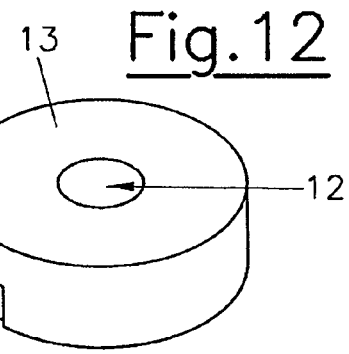
FIG. 12 shows the ring of the sensor device of FIG. 8 in an oblique view.

The holder 4 is inserted into the interior of the cylindrical guiding and protecting element 3. The holder 4 together with the resonator element 30 is thus guided and protected from external influences. FIGS. 6 and 7 show details of the guiding and protecting element 3.

The sensor housing 2 of the sensor device 1 is attached to a pipe system 11 via a gas-tight welded cutting-ring fitting.

FIGS. 8 to 12 show a second variant of a sensor device 1. The sensor housing 2 of the sensor device 1 comprises a first 2a, a second 2b and a third 2c sensor housing part. As in the first variant shown in FIGS. 1 to 7, a holder 4 with a clamping element 7 (not visible here) and a cylindrical guiding and protecting element 3 are employed for guiding and lateral contacting of the resonator element 30. The holder 4 and the cylindrical guiding and protecting element 3 are glued into a bore 12 of a ceramic ring 13. The main surfaces of the ring 13 act as sealing faces.

The sensor housing 2 comprises three sensor housing parts. The second 2b and the third 2c sensor housing part are fixedly joined, for instance by welding. The ring 13, together with the cylindrical guiding and protecting element 3 and the holder 4 with the sensor element 30, is inserted into the second part 2b. The third sensor housing part 2c is a welding nipple and is welded to the pipe system 11. The first sensor housing part 2a is a covering cap, which is screwed onto the second housing part 2b by means of a thread 14. Copper sealing rings 15, 16 are used as additional sealing elements.

Figure 13:
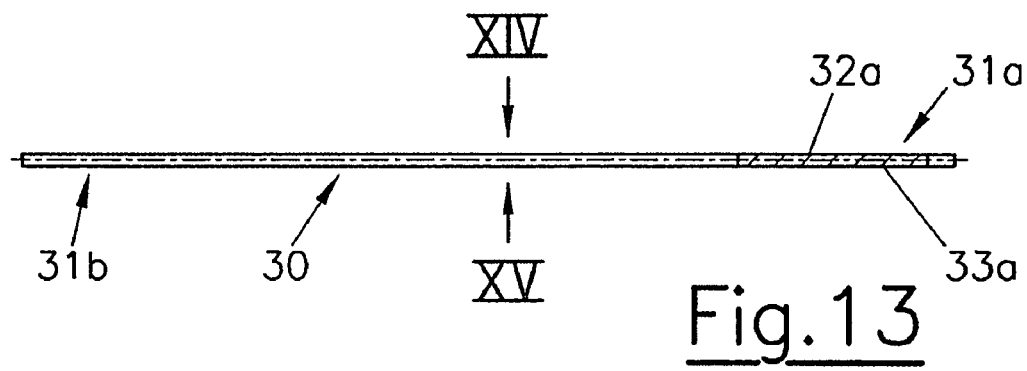
FIG. 13 shows a piezoelectric sensor element in a side view as indicated by arrow XIII in FIG. 14.
Figure 14:
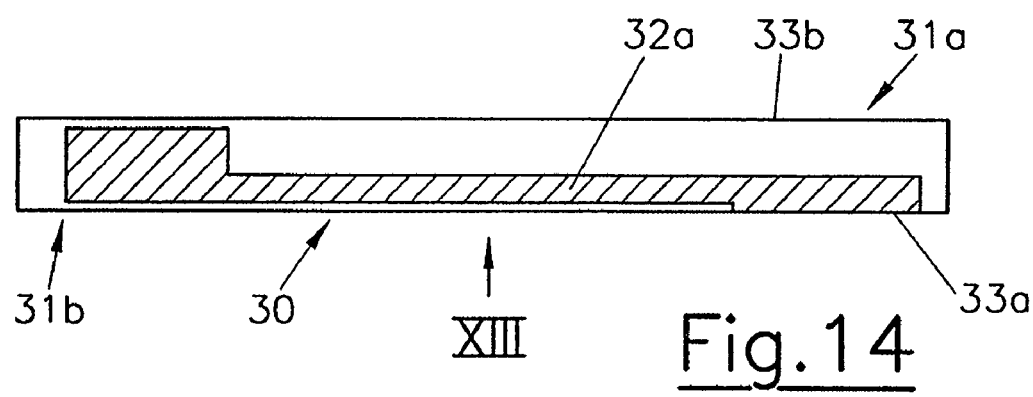
FIG. 14 shows the sensor element in a view as indicated by arrow XIV of FIG. 13.
Figure 15:
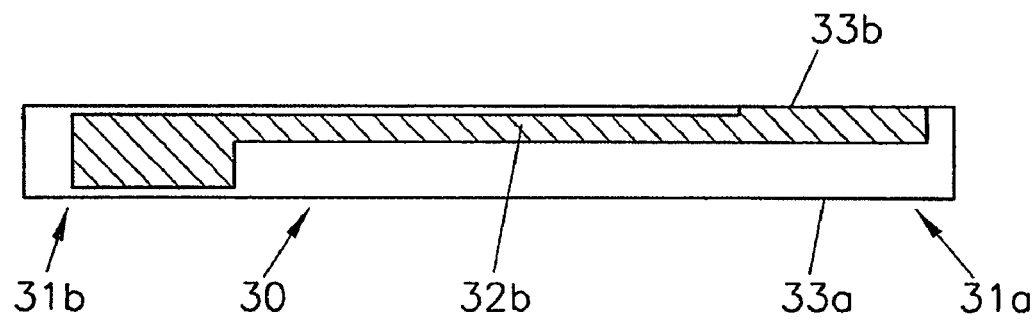
FIG. 15 shows the sensor element in a view as indicated by arrow XV of FIG. 13.

FIGS. 13 to 15 show a resonator element 30 with coating, constituted by a $GaPO_4$ strip resonator. Reference number 31a indicates the contact region clamped in the holder 4. The measuring region 31b is subjected to the gas stream to be measured. The shaded area indicates electrodes 32a, 32b, for instance platinum electrodes, extending from the measuring region 31b to the contact region 31a and to the edges 33a, 33b. Electrical contacting is effected at the edges 33a, 33b by the first and the second arm 7a and 7b. In the measuring region 31b a catalytic nickel layer is provided.

The invention claimed is:

1. A piezoelectric sensor device comprising a sensor housing, a piezoelectric sensor element, and a holder for holding the piezoelectric sensor element, wherein the holder is configured as a clamping element which has at least one elastic first arm for clamped holding of a contact region of said piezoelectric sensor element, wherein the piezoelectric sensor element consists of an elongated and essentially strip-shaped piezoelectric resonator element which defines a contact region in contact with the elastic first arm and a measuring region longitudinally extending from the contact region which freely projects into a fluid stream to be measured.

2. The sensor device according to claim 1, wherein the clamping device comprises an elastic or non-elastic second arm.

3. The sensor device according to claim 2, wherein the first arm spaced a distance from the second arm, such that the piezoelectric resonator element is insertable between the first and the second arm of the holder.

4. The sensor device according to claim 2, wherein the first and the second arm protrude in axial direction from a base plate of the holder.

5. The sensor device according to claim 1, wherein the holder is at least partially insertable into a guiding and protecting element.

6. The sensor device according to claim 5, wherein the guiding and protecting element is insertable into the sensor housing.

7. The sensor device according to claim 6, wherein the guiding and protecting element is insertable into a hollow, cylindrical second sensor housing part.

8. The sensor device according to claim 5, wherein the guiding and protecting element is inserted into a bore of a ring, and wherein the ring is inserted into a second sensor housing part of the sensor housing.

9. The sensor device according to claim 8, wherein the ring is a ceramic ring.

10. The sensor device according to claim 8, wherein the guiding and protecting element is partly located in a third sensor housing part configured as a welding nipple, which is joined to a second sensor housing part receiving the ring.

11. The sensor device according to claim 8, wherein the first sensor housing part is configured as a covering cap.

12. The sensor device according to claim 1, wherein the sensor housing has a first and a second housing part, which are joined by a threaded connection.

13. The sensor device according to claim 1, wherein at least one of the first and second arm of the clamping device is curved.

14. The sensor device according to claim 1, wherein the holder consists of glass ceramic material.

15. The sensor device according to claim 1, wherein the guiding and protecting element consists of glass ceramic material.

16. The sensor device according to claim 1, wherein the sensor housing consists of metal.

17. The sensor device according to claim 1, wherein the holder is high-temperature-resistant and gas-tight.

18. The sensor device according to claim 1, combined with a microbalance.

* * * * *